(12) United States Patent
Yi et al.

(10) Patent No.: US 9,568,456 B2
(45) Date of Patent: Feb. 14, 2017

(54) PEPTIDE SELECTIVELY BINDING TO VOLATILE ORGANIC COMPOUNDS

(71) Applicant: KOREA INSTITUTE OF SCIENCE AND TECHNOLOGY, Seoul (KR)

(72) Inventors: Hyunjung Yi, Seoul (KR); Sang Kyung Kim, Seoul (KR); Soomi Ju, Seoul (KR); Ki Young Lee, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 0 days.

(21) Appl. No.: 14/737,648

(22) Filed: Jun. 12, 2015

(65) Prior Publication Data
US 2016/0103108 A1 Apr. 14, 2016

(30) Foreign Application Priority Data

Oct. 8, 2014 (KR) ........................ 10-2014-0135861
Mar. 11, 2015 (KR) ........................ 10-2015-0034036

(51) Int. Cl.
| C07K 7/06 | (2006.01) |
| G01N 33/00 | (2006.01) |
| G01N 29/02 | (2006.01) |
| G01N 29/036 | (2006.01) |
| C07K 14/005 | (2006.01) |

(52) U.S. Cl.
CPC ............ *G01N 33/0004* (2013.01); *C07K 7/06* (2013.01); *C07K 14/005* (2013.01); *G01N 29/022* (2013.01); *G01N 29/036* (2013.01); *C12N 2795/14122* (2013.01); *G01N 2291/0256* (2013.01)

(58) Field of Classification Search
CPC ............ G01N 33/0004; G01N 29/022; G01N 2291/0256; G01N 29/036; C07K 7/06; C07K 14/005; C12N 2795/14122
See application file for complete search history.

(56) References Cited

U.S. PATENT DOCUMENTS 7,504,490 B1 * 3/2009 Weinstock ............ C07K 14/38
435/252.3

OTHER PUBLICATIONS

ATPase-*Bradyrhizobium* sp. DOA9, from http://www.ncbi.nlm.nih.gov/protein/640605677?report=genbank&log$=prottop&blast_ra . . . , pp. 1-2, accessed May 27, 2016.*
Becker et al, Head Morphogenesis Genes of the Bacillus subtilis Bacteriophage SPP1, J. Mol. Biol., 1997, 268, pp. 822-839.*
Becket et al coat protein G13P sequence, from STN search, p. 1, accessed May 24, 2016.*
Protein CBR-TAF-1, from http://www.ncbi.nlm.nih.gov/protein/309359728?report=genbank&log$=prottop&blast_ra . . . , pages 1-3, accessed May 27, 2016.*
Iannolo et al, Modifying Filamentous Phage Capsid: Limits in the Size of the Major Capsid Protein, J. Mol. Biol., 1995, 248, pp. 835-844.*
Imai et al, Effect of protein properties on display efficiency using the M13 phage display system, Pharmazie, 2008, 63, pp. 760-764.*
Volatile organic compounds, from http://www.atsdr.cdc.gov/substances/toxchemicallisting.asp?sysid=7, pp. 1-2, accessed May 27, 2016.*
Yampolsky et al, The Exchangeability of Amino Acids in Proteins, Genetics, 2005, 170, pp. 1459-1472.*
Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*

* cited by examiner

*Primary Examiner* — Julie Ha
*Assistant Examiner* — Li Ni Komatsu
(74) *Attorney, Agent, or Firm* — Goldilocks Zone IP Law

(57) ABSTRACT

Provided is a peptide selectively binding to a volatile organic compound, in which the peptide has excellent selectivity for the volatile organic compound and has stability at room temperature so as to effectively collect and detect or eliminate the volatile organic compound.

7 Claims, 8 Drawing Sheets

| LEGEND | | |
|---|---|---|
| PEPTIDE | SEQUENCE | SEQUENCE IDENTIFIER |
| BP2 | HSSPVGA | SEQ ID NO: 18 |
| BP3 | SKYSPDT | SEQ ID NO: 19 |
| BP4 | HDSSNMA | SEQ ID NO: 20 |
| BP5 | HNSGLAA | SEQ ID NO: 21 |
| BP6 | DTSSAIP | SEQ ID NO: 22 |
| BP7 | RETQSFS | SEQ ID NO: 23 |
| BP8 | TYVTYDG | SEQ ID NO: 24 |
| BP9 | YDGTASS | SEQ ID NO: 25 |
| BP10 | AGYNSSA | SEQ ID NO: 26 |
| BP11 | YSSPVGA | SEQ ID NO: 27 |
| BP12 | SGTDYGP | SEQ ID NO: 28 |

| LEGEND | | |
|---|---|---|
| PEPTIDE | SEQUENCE | SEQUENCE IDENTIFIER |
| BP1 | RNESSVP | SEQ ID NO: 17 |

SEQUENCE LISTING

<160> NUMBER OF SEQ ID NOS: 38

<210> SEQ ID NO 1
<211> LENGTH: 7
<212> TYPE: PRT
<213> ORGANISM: Artificial Sequence
<220> FEATURE:
<223> OTHER INFORMATION: BP1 which is a peptide selectively binding to
      volatile organic compounds
<220> FEATURE:
<221> NAME/KEY: VARIANT
<222> LOCATION: (2)..(3)
<223> OTHER INFORMATION: X is D, E, N or Q
<220> FEATURE:
<221> NAME/KEY: VARIANT
<222> LOCATION: (6)..(6)
<223> OTHER INFORMATION: X is I, L, or V

<400> SEQUENCE: 1

Arg Xaa Xaa Ser Ser Xaa Pro
1               5

<210> SEQ ID NO 2
<211> LENGTH: 7
<212> TYPE: PRT
<213> ORGANISM: Artificial Sequence
<220> FEATURE:
<223> OTHER INFORMATION: BP2 which is a peptide selectively binding to
      volatile organic compounds
<220> FEATURE:
<221> NAME/KEY: VARIANT
<222> LOCATION: (1)..(1)
<223> OTHER INFORMATION: X is W, Y, F or H
<220> FEATURE:
<221> NAME/KEY: VARIANT
<222> LOCATION: (5)..(5)
<223> OTHER INFORMATION: X is I, L, or V

<400> SEQUENCE: 2

Xaa Ser Ser Pro Xaa Gly Ala
1               5

<210> SEQ ID NO 3
<211> LENGTH: 7
<212> TYPE: PRT
<213> ORGANISM: Artificial Sequence
<220> FEATURE:
<223> OTHER INFORMATION: BP3 which is a peptide selectively binding to
      volatile organic compounds
<220> FEATURE:
<221> NAME/KEY: VARIANT
<222> LOCATION: (3)..(3)
<223> OTHER INFORMATION: X is W, Y, F or H
<220> FEATURE:
<221> NAME/KEY: VARIANT
<222> LOCATION: (6)..(6)
<223> OTHER INFORMATION: X is D, E, N, or Q

<400> SEQUENCE: 3

Ser Lys Xaa Ser Pro Xaa Thr
1               5

<210> SEQ ID NO 4
<211> LENGTH: 7
<212> TYPE: PRT
<213> ORGANISM: Artificial Sequence
<220> FEATURE:
<223> OTHER INFORMATION: BP4 which is a peptide selectively binding to
      volatile organic compounds
<220> FEATURE:
<221> NAME/KEY: VARIANT
<222> LOCATION: (1)..(1)

```
<223> OTHER INFORMATION: X is W, Y, F or H
<220> FEATURE:
<221> NAME/KEY: VARIANT
<222> LOCATION: (2)..(2)
<223> OTHER INFORMATION: X is D, E, N, or Q
<220> FEATURE:
<221> NAME/KEY: VARIANT
<222> LOCATION: (5)..(5)
<223> OTHER INFORMATION: X is D, E, N, or Q

<400> SEQUENCE: 4

Xaa Xaa Ser Ser Xaa Met Ala
1               5

<210> SEQ ID NO 5
<211> LENGTH: 7
<212> TYPE: PRT
<213> ORGANISM: Artificial Sequence
<220> FEATURE:
<223> OTHER INFORMATION: BP5 which is a peptide selectively binding to
      volatile organic compounds
<220> FEATURE:
<221> NAME/KEY: VARIANT
<222> LOCATION: (1)..(1)
<223> OTHER INFORMATION: X is W, Y, F or H
<220> FEATURE:
<221> NAME/KEY: VARIANT
<222> LOCATION: (2)..(2)
<223> OTHER INFORMATION: X is D, E, N or Q
<220> FEATURE:
<221> NAME/KEY: VARIANT
<222> LOCATION: (5)..(5)
<223> OTHER INFORMATION: X is I, L, or V

<400> SEQUENCE: 5

Xaa Xaa Ser Gly Xaa Ala Ala
1               5

<210> SEQ ID NO 6
<211> LENGTH: 7
<212> TYPE: PRT
<213> ORGANISM: Artificial Sequence
<220> FEATURE:
<223> OTHER INFORMATION: BP6 which is a peptide selectively binding to
      volatile organic compounds
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (6)..(6)
<223> OTHER INFORMATION: X is I, L, or V

<400> SEQUENCE: 6

Xaa Thr Ser Ser Ala Xaa Pro
1               5

<210> SEQ ID NO 7
<211> LENGTH: 7
<212> TYPE: PRT
<213> ORGANISM: Artificial Sequence
<220> FEATURE:
<223> OTHER INFORMATION: BP7 which is a peptide selectively binding to
      volatile organic compounds
<220> FEATURE:
<221> NAME/KEY: VARIANT
<222> LOCATION: (2)..(2)
<223> OTHER INFORMATION: X is D, E, N or Q
<220> FEATURE:
<221> NAME/KEY: VARIANT
<222> LOCATION: (4)..(4)
<223> OTHER INFORMATION: X is D, E, N or Q
```

```
<400> SEQUENCE: 7

Arg Xaa Thr Xaa Ser Phe Ser
1               5

<210> SEQ ID NO 8
<211> LENGTH: 7
<212> TYPE: PRT
<213> ORGANISM: Artificial Sequence
<220> FEATURE:
<223> OTHER INFORMATION: BP8 which is a peptide selectively binding to
      volatile organic compounds
<220> FEATURE:
<221> NAME/KEY: VARIANT
<222> LOCATION: (2)..(2)
<223> OTHER INFORMATION: X is W, Y, F or H
<220> FEATURE:
<221> NAME/KEY: VARIANT
<222> LOCATION: (3)..(3)
<223> OTHER INFORMATION: X is I, L, or V
<220> FEATURE:
<221> NAME/KEY: VARIANT
<222> LOCATION: (5)..(5)
<223> OTHER INFORMATION: X is W, Y, F or H
<220> FEATURE:
<221> NAME/KEY: VARIANT
<222> LOCATION: (6)..(6)
<223> OTHER INFORMATION: X is D, E, N or Q

<400> SEQUENCE: 8

Thr Xaa Xaa Thr Xaa Xaa Gly
1               5

<210> SEQ ID NO 9
<211> LENGTH: 7
<212> TYPE: PRT
<213> ORGANISM: Artificial Sequence
<220> FEATURE:
<223> OTHER INFORMATION: BP9 which is a peptide selectively binding to
      volatile organic compounds
<220> FEATURE:
<221> NAME/KEY: VARIANT
<222> LOCATION: (1)..(1)
<223> OTHER INFORMATION: X is W, Y, F or H
<220> FEATURE:
<221> NAME/KEY: VARIANT
<222> LOCATION: (2)..(2)
<223> OTHER INFORMATION: X is D, E, N or Q

<400> SEQUENCE: 9

Xaa Xaa Gly Thr Ala Ser Ser
1               5

<210> SEQ ID NO 10
<211> LENGTH: 7
<212> TYPE: PRT
<213> ORGANISM: Artificial Sequence
<220> FEATURE:
<223> OTHER INFORMATION: BP10 which is a peptide selectively binding to
      volatile organic compounds
<220> FEATURE:
<221> NAME/KEY: VARIANT
<222> LOCATION: (3)..(3)
<223> OTHER INFORMATION: X is W, Y, F or H
<220> FEATURE:
<221> NAME/KEY: VARIANT
<222> LOCATION: (4)..(4)
<223> OTHER INFORMATION: X is D, E, N, or Q

<400> SEQUENCE: 10

Ala Gly Xaa Xaa Ser Ser Ala
1               5
```

```
<210> SEQ ID NO 11

<400> SEQUENCE: 11

000

<210> SEQ ID NO 12
<211> LENGTH: 7
<212> TYPE: PRT
<213> ORGANISM: Artificial Sequence
<220> FEATURE:
<223> OTHER INFORMATION: BP12 which is a peptide selectively binding to
      volatile organic compounds
<220> FEATURE:
<221> NAME/KEY: VARIANT
<222> LOCATION: (4)..(4)
<223> OTHER INFORMATION: X is D, E, N or Q
<220> FEATURE:
<221> NAME/KEY: VARIANT
<222> LOCATION: (5)..(5)
<223> OTHER INFORMATION: X is W, Y, F or H

<400> SEQUENCE: 12

Ser Gly Thr Xaa Xaa Gly Pro
1               5

<210> SEQ ID NO 13
<211> LENGTH: 7
<212> TYPE: PRT
<213> ORGANISM: Artificial Sequence
<220> FEATURE:
<223> OTHER INFORMATION: TP1 which is a peptide selectively binding to
      volatile organic compounds
<220> FEATURE:
<221> NAME/KEY: VARIANT
<222> LOCATION: (3)..(3)
<223> OTHER INFORMATION: X is D, E, N or Q
<220> FEATURE:
<221> NAME/KEY: VARIANT
<222> LOCATION: (4)..(4)
<223> OTHER INFORMATION: X is I, L, or V
<220> FEATURE:
<221> NAME/KEY: VARIANT
<222> LOCATION: (5)..(5)
<223> OTHER INFORMATION: X is D, E, N or Q
<220> FEATURE:
<221> NAME/KEY: VARIANT
<222> LOCATION: (7)..(7)
<223> OTHER INFORMATION: X is I, L, or V

<400> SEQUENCE: 13

Ser Arg Xaa Xaa Xaa Met Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: TP2 which is a peptide selectively binding to
      volatile organic compounds
<220> FEATURE:
<221> NAME/KEY: VARIANT
<222> LOCATION: (1)..(1)
<223> OTHER INFORMATION: X is D, E, N or Q
<220> FEATURE:
<221> NAME/KEY: VARIANT
<222> LOCATION: (3)..(3)
<223> OTHER INFORMATION: X is I, L, or V
<220> FEATURE:
<221> NAME/KEY: VARIANT
<222> LOCATION: (6)..(6)
```

<223> OTHER INFORMATION: X is I, L, or V

<400> SEQUENCE: 14

Xaa Pro Xaa Pro Thr Xaa Pro
1               5

<210> SEQ ID NO 15
<211> LENGTH: 7
<212> TYPE: PRT
<213> ORGANISM: Artificial Sequence
<220> FEATURE:
<223> OTHER INFORMATION: TP3 which is a peptide selectively binding to
      volatile organic compounds
<220> FEATURE:
<221> NAME/KEY: VARIANT
<222> LOCATION: (2)..(2)
<223> OTHER INFORMATION: X is D, E, N or Q

<400> SEQUENCE: 15

Gly Xaa Met Met Ala Ala Pro
1               5

<210> SEQ ID NO 16
<211> LENGTH: 7
<212> TYPE: PRT
<213> ORGANISM: Artificial Sequence
<220> FEATURE:
<223> OTHER INFORMATION: TP4 which is a peptide selectively binding to
      volatile organic compounds
<220> FEATURE:
<221> NAME/KEY: VARIANT
<222> LOCATION: (1)..(1)
<223> OTHER INFORMATION: X is D, E, N or Q
<220> FEATURE:
<221> NAME/KEY: VARIANT
<222> LOCATION: (4)..(4)
<223> OTHER INFORMATION: X is D, E, N or Q
<220> FEATURE:
<221> NAME/KEY: VARIANT
<222> LOCATION: (6)..(6)
<223> OTHER INFORMATION: X is I, L, or V

<400> SEQUENCE: 16

Xaa Ser Ala Xaa Pro Xaa Pro
1               5

<210> SEQ ID NO 17
<211> LENGTH: 7
<212> TYPE: PRT
<213> ORGANISM: Artificial Sequence
<220> FEATURE:
<223> OTHER INFORMATION: BP1 which is a peptide selectively binding to
      volatile organic compounds

<400> SEQUENCE: 17

Arg Asn Glu Ser Ser Val Pro
1               5

<210> SEQ ID NO 18
<211> LENGTH: 7
<212> TYPE: PRT
<213> ORGANISM: Artificial Sequence
<220> FEATURE:
<223> OTHER INFORMATION: BP2 which is a peptide selectively binding to
      volatile organic compounds 2

<400> SEQUENCE: 18

His Ser Ser Pro Val Gly Ala
1               5

<210> SEQ ID NO 19
<211> LENGTH: 7
<212> TYPE: PRT
<213> ORGANISM: Artificial Sequence
<220> FEATURE:
<223> OTHER INFORMATION: BP3 which is a peptide selectively binding to
      volatile organic compounds

<400> SEQUENCE: 19

Ser Lys Tyr Ser Pro Asp Thr
1               5

<210> SEQ ID NO 20
<211> LENGTH: 7
<212> TYPE: PRT
<213> ORGANISM: Artificial Sequence
<220> FEATURE:
<223> OTHER INFORMATION: BP4 which is a peptide selectively binding to
      volatile organic compounds

<400> SEQUENCE: 20

His Asp Ser Ser Asn Met Ala
1               5

<210> SEQ ID NO 21
<211> LENGTH: 7
<212> TYPE: PRT
<213> ORGANISM: Artificial Sequence
<220> FEATURE:
<223> OTHER INFORMATION: BP5 which is a peptide selectively binding to
      volatile organic compounds

<400> SEQUENCE: 21

His Asn Ser Gly Leu Ala Ala
1               5

<210> SEQ ID NO 22
<211> LENGTH: 7
<212> TYPE: PRT
<213> ORGANISM: Artificial Sequence
<220> FEATURE:
<223> OTHER INFORMATION: BP6 which is a peptide selectively binding to
      volatile organic compounds

<400> SEQUENCE: 22

Asp Thr Ser Ser Ala Ile Pro
1               5

<210> SEQ ID NO 23
<211> LENGTH: 7
<212> TYPE: PRT
<213> ORGANISM: Artificial Sequence
<220> FEATURE:
<223> OTHER INFORMATION: BP7 which is a peptide selectively binding to
      volatile organic compounds

<400> SEQUENCE: 23

Arg Glu Thr Gln Ser Phe Ser
1               5

<210> SEQ ID NO 24
<211> LENGTH: 7
<212> TYPE: PRT
<213> ORGANISM: Artificial Sequence
<220> FEATURE:
<223> OTHER INFORMATION: BP8 which is a peptide selectively binding to
      volatile organic compounds

```
<400> SEQUENCE: 24

Thr Tyr Val Thr Tyr Asp Gly
1               5

<210> SEQ ID NO 25
<211> LENGTH: 7
<212> TYPE: PRT
<213> ORGANISM: Artificial Sequence
<220> FEATURE:
<223> OTHER INFORMATION: BP9 which is a peptide selectively binding to
      volatile organic compounds

<400> SEQUENCE: 25

Tyr Asp Gly Thr Ala Ser Ser
1               5

<210> SEQ ID NO 26
<211> LENGTH: 7
<212> TYPE: PRT
<213> ORGANISM: Artificial Sequence
<220> FEATURE:
<223> OTHER INFORMATION: BP10 which is a peptide selectively binding to
      volatile organic compounds

<400> SEQUENCE: 26

Ala Gly Tyr Asn Ser Ser Ala
1               5

<210> SEQ ID NO 27
<211> LENGTH: 7
<212> TYPE: PRT
<213> ORGANISM: Artificial Sequence
<220> FEATURE:
<223> OTHER INFORMATION: BP11 which is a peptide selectively binding to
      volatile organic compounds

<400> SEQUENCE: 27

Tyr Ser Ser Pro Val Gly Ala
1               5

<210> SEQ ID NO 28
<211> LENGTH: 7
<212> TYPE: PRT
<213> ORGANISM: Artificial Sequence
<220> FEATURE:
<223> OTHER INFORMATION: BP12 which is a peptide selectively binding to
      volatile organic compounds

<400> SEQUENCE: 28

Ser Gly Thr Asp Tyr Gly Pro
1               5

<210> SEQ ID NO 29
<211> LENGTH: 7
<212> TYPE: PRT
<213> ORGANISM: Artificial Sequence
<220> FEATURE:
<223> OTHER INFORMATION: TP1 which is a peptide selectively binding to
      volatile organic compounds

<400> SEQUENCE: 29

Ser Arg Asn Val Asp Met Val
1               5

<210> SEQ ID NO 30
<211> LENGTH: 7
<212> TYPE: PRT
```

```
<213> ORGANISM: Artificial Sequence
<220> FEATURE:
<223> OTHER INFORMATION: TP2 which is a peptide selectively binding to
      volatile organic compounds

<400> SEQUENCE: 30

Asn Pro Leu Pro Thr Leu Pro
1               5

<210> SEQ ID NO 31
<211> LENGTH: 7
<212> TYPE: PRT
<213> ORGANISM: Artificial Sequence
<220> FEATURE:
<223> OTHER INFORMATION: TP3 which is a peptide selectively binding to
      volatile organic compounds

<400> SEQUENCE: 31

Gly Asp Met Met Ala Ala Pro
1               5

<210> SEQ ID NO 32
<211> LENGTH: 7
<212> TYPE: PRT
<213> ORGANISM: Artificial Sequence
<220> FEATURE:
<223> OTHER INFORMATION: TP4 which is a peptide selectively binding to
      volatile organic compounds

<400> SEQUENCE: 32

Glu Ser Ala Asp Pro Ile Pro
1               5

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38
<211> LENGTH: 50
<212> TYPE: PRT
<213> ORGANISM: M13 phage
<220> FEATURE:
```

```
<223> OTHER INFORMATION: P8 protein

<400> SEQUENCE: 38

Ala Glu Gly Asp Asp Pro Ala Lys Ala Ala Phe Asn Ser Leu Gln Ala
1               5                   10                  15

Ser Ala Thr Glu Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45

Ala Ser
    50
```

PEPTIDE SELECTIVELY BINDING TO VOLATILE ORGANIC COMPOUNDS

CROSS-REFERENCE TO RELATED APPLICATIONS

This application claims the benefit of Korean Patent Application No: 10-2014-0135861, filed on Oct. 8, 2014, and Korean Patent Application No: 10-2015-0034036, filed on Mar. 11, 2015, in the Korean Intellectual Property Office, the disclosures of which are incorporated herein in their entireties by reference.

BACKGROUND

1. Field

The present disclosure relates to a novel peptide selectively binding to a volatile organic compound.

2. Description of the Related Art

Volatile organic compounds (VOCs) are environmental factors highly dangerous to health, and for example, continuous inhalation of excessive benzene is known to cause leukemia.

A variety of gas sensors have been studied to detect such dangerous volatile organic compounds. The developed gas sensors work at room temperature with high sensitivity, but have a problem of very low selectivity. To overcome this problem, various molecules have been developed. As a receptor for detecting volatile organic compounds, metal ligand molecules have been reported. The metal ligand molecules, metalloporphyrins are used in fabrication of various metal array sensors to detect fluorescence image patterns which are observed during reaction. This type of sensor is developed not by using selective receptors but by applying the principle of previous thin film sensors, and its selectivity is low.

In a selective receptor screening method, a target molecule is immobilized on the surface, and thus it is difficult to apply this method to screening of gas molecules. Until now, there have been no reports of selective receptors for volatile organic compounds such as benzene or toluene molecules. Accordingly, there is a demand for a technique which has excellent selectivity for volatile organic compounds and has stability at room temperature to effectively collect volatile organic compounds in air, such as benzene or toluene.

SUMMARY

An aspect provides a peptide or peptide set including one or more selected from the group consisting of amino acid sequences of $RX_2X_2SSX_3P$ (SEQ ID NO: 1), $X_1SSPX_3GA$ (SEQ ID NO: 2), $SKX_1SPX_2T$ (SEQ ID NO: 3), $X_1X_2SSX_2MA$ (SEQ ID NO: 4), $X_1X_2SGX_3AA$ (SEQ ID NO: 5), $X_2TSSAX_3P$ (SEQ ID NO: 6), $RX_2TX_2SFS$ (SEQ ID NO: 7), $TX_1X_3TX_1X_2G$ (SEQ ID NO: 8), $X_1X_2GTASS$ (SEQ ID NO: 9), $AGX_1X_2SSA$ (SEQ ID NO: 10), $SGTX_2X_1GP$ (SEQ ID NO: 12), $SRX_2X_3X_2MX_3$ (SEQ ID NO: 13), $X_2PX_3PTX_3P$ (SEQ ID NO: 14), $GX_2MMAAP$ (SEQ ID NO: 15), and $X_2SAX_2PX_3P$ (SEQ ID NO: 16). In the peptide, X1 may be W, Y, F or H, X2 may be D, E, N or Q, and X3 may be I, L or V.

Another aspect provides a device of detecting or eliminating volatile organic compounds including the peptide or peptide set.

Still another aspect provides a method of detecting or eliminating volatile organic compounds in a sample, including contacting the peptide or peptide set with the sample.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
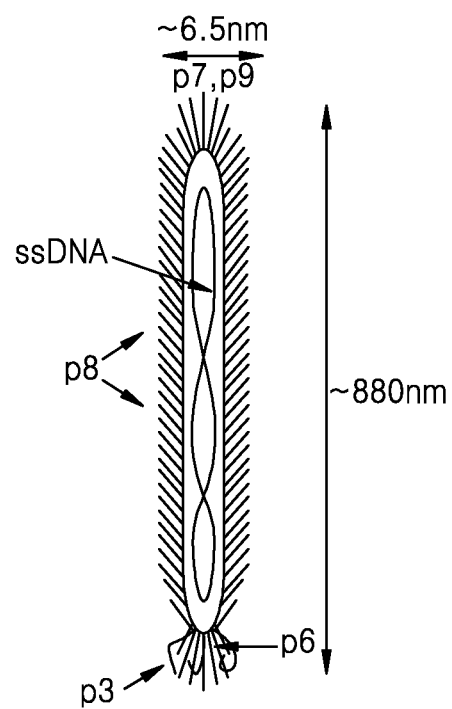
FIG. 1 is a schematic illustration showing a structure of M13 phage according to a specific embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the exemplary embodiments are merely described below, by referring to the figures, to explain aspects of the present description.

An aspect provides a peptide or peptide set including one or more selected from the group consisting of amino acid sequences of $RX_2X_2SSX_3P$ (SEQ ID NO: 1), $X_1SSPX_3GA$ (SEQ ID NO: 2), $SKX_1SPX_2T$ (SEQ ID NO: 3), $X_1X_2SSX_2MA$ (SEQ ID NO: 4), $X_1X_2SGX_3AA$ (SEQ ID NO: 5), $X_2TSSAX_3P$ (SEQ ID NO: 6), $RX_2TX_2SFS$ (SEQ ID NO: 7), $TX_1X_3TX_1X_2G$ (SEQ ID NO: 8), $X_1X_2GTASS$ (SEQ ID NO: 9), $AGX_1X_2SSA$ (SEQ ID NO: 10), $SGTX_2X_1GP$ (SEQ ID NO: 12), $SRX_2X_3X_2MX_3$(SEQ ID NO: 13), $X_2PX_3PTX_3P$ (SEQ ID NO: 14), $GX_2MMAAP$ (SEQ ID NO: 15), and $X_2SAX_2PX_3P$ (SEQ ID NO: 16). In the peptide, X1 may be W, Y, F or H, X2 may be D, E, N or Q, and X3 may be I, L or V.

Further, the peptide or peptide set may be a peptide or peptide set including one or more selected from the group consisting of amino acid sequences of SEQ ID NOS. 17 to 32.

Consecutive amino acid sequences of a coat protein of a phage may be linked to the N-terminus or C-terminus of the amino acid sequence of the peptide or peptide set. Therefore, for example, the peptide or peptide set may have an amino acid sequence having a length of 5 to 60, 7 to 55, 7 to 40, 7 to 30, 7 to 20, or 7 to 10 amino acids.

The peptide may have a conservative substitution of a known peptide. As used herein, the term "conservative substitution" denotes replacement of a first amino acid residue by a second different amino acid residue without changing biophysical properties of a protein or a peptide. Here, the first and second amino acid residues mean those having side chains having similar biophysical properties. The similar biophysical properties may include an ability to donate or accept hydrophobicity, charge, polarity, or hydrogen bonding. Examples of the conservative substitution may be within the groups of basic amino acids (arginine, lysine, and histidine), acidic amino acids (glutamic acid and aspartic acid), polar amino acids (glutamine and asparagine), hydrophobic amino acids (leucine, isoleucine, valine and methionine), hydrophilic amino acids (aspartic acid, glutamic acid, asparagine and glutamine), aromatic amino acids (phenylalanine, tryptophan, tyrosine and histidine), and small amino acids (glycine, alanine, serine and threonine). Amino acid substitutions that do not generally alter specific activity are known in the art. For example, in the peptide, X1 may be W, Y, F or H, X2 may be D, E, N or Q, and X3 may be I, L or V.

The peptide or peptide set may optionally bind to a volatile organic compound.

As used herein, the term "volatile organic compound" may refer to a liquid, gas, or solid organic compound that is continuously volatilized and discharged into the air at a predetermined temperature and pressure, and may include organic compounds that exist as gases at a room temperature or atmospheric pressure, such as hydrocarbons composed of carbon and hydrogen, halogenated hydrocarbons, or nitrogen- or sulfur-containing hydrocarbons.

The volatile organic compound may be hydrocarbons containing aromatic groups. The hydrocarbons containing aromatic groups may be hydrocarbons containing benzene rings. The hydrocarbons containing benzene rings may be hydrocarbons, in which at least one hydrogen atom of the benzene is substituted by $C_1$ to $C_{10}$ alkyl group, alkenyl group, or alkynyl group. Further, the hydrocarbons containing benzene rings may be $C_6$ to $C_7$ hydrocarbons.

Examples of the volatile organic compound may include acetaldehyde, acetylene, acetylene dichloride, acrolein, acrylonitrile, benzene, 1,3-butadiene, butane, 1-butene, 2-butene, carbon tetrachloride, chloroform, cyclohexane, 1,2-dichloroethane, diethylamine, dimethylamine, ethylene, formaldehyde, n-hexane, isopropyl alcohol, methanol, methyl ethyl ketone, methylene chloride, MTBE, propylene, propyleneoxide, 1,1,1-trichloroethane, trichloroethylene, gasoline, naphtha, crude oil, acetic acid, ethylbenzene, nitrobenzene, toluene, tetrachloroethylene, xylene or styrene.

The peptide or peptide set may be those displayed on the coat protein of the phage or the fragment thereof. The peptide or peptide set, or the phage may be those bound to the graphitic material. The peptide, phage and graphitic material are the same as described above.

The term "phage" or "bacteriophage" is used interchangeably, and may refer to a virus that infects bacteria and replicates within the bacteria. The phage or bacteriophage may be used to display a peptide which selectively or specifically binds to a graphitic material or volatile organic compound. The phage may be genetically engineered to display the peptide capable of binding to the graphitic material on a coat protein of the phage or a fragment thereof. As used herein, the term "genetic engineering" or "genetically engineered" means introduction of one or more genetic modifications into the phage in order to display the peptide capable of binding to the graphitic material on the coat protein of the phage or the fragment thereof, or a phage prepared thereby. The genetic modifications include introduction of a foreign gene encoding the peptide. The phage may be a filamentous phage, for example, M13 phage, F1 phage, Fd phage, If1 phage, Ike phage, Zj/Z phage, Ff phage, Xf phage, Pf1 phage, or Pf3 phage.

As used herein, the term "phage display" may refer to a display of a functional foreign peptide or protein on the surface of a phage or phagemid particle. The surface of the phage may refer to a coat protein of the phage or a fragment thereof. Further, the phage may be a phage in which the C-terminus of the functional foreign peptide is linked to the N-terminus of the coat protein of the phage, or the peptide is inserted between consecutive amino acid sequences of the coat protein of the phage or replaced for a part of the consecutive amino acid sequences of the coat protein. The positions in the amino acid sequence of the coat protein, at which the peptide is inserted or replaced, may be positions of 1 to 5, positions of 1 to 40, positions of 1 to 30, positions of 1 to 20, position of 1 to 10, positions of 2 to 8, positions of 2 to 4, positions of 2 to 3, positions of 3 to 4, or a position of 2 from the N-terminus of the coat protein. Further, the coat protein may be p3, p6, p8 or p9. For example, the C-terminus of any one peptide of SEQ ID NO: 1 to SEQ ID NO: 8 may be linked to the body of M13 phage, that is, not to the tip of the phage, but to the N-terminus of p8 (SEQ ID NO: 19) having a length of 50 amino acids, which is present on the body in a longitudinal direction. Further, for example, any one peptide of SEQ ID NO: 1 to SEQ ID NO: 8 may be replaced for the positions of 2 to 4 (e.g., EGD), the positions of 2 to 3 or 3 to 4, or the position of 2 in the amino acid sequence of the coat protein p8 of M13 phage.

The peptide binding to the volatile organic compound may be selected from peptide libraries, for example, by a phage display technique. Through the phage display technique, the peptide may be genetically linked to, inserted into, or substituted for the coat protein of the phage, resulting in display of the protein on the exterior of phage, in which the peptide may be encoded by genetic information in the virion. Vast numbers of variants of the protein may be selected and screened by the displayed protein and DNA encoding the same, this method is called "biopanning". Briefly, biopanning is carried out by incubating the pool of phage-displayed variants with a target (e.g., graphitic material) that has been immobilized, washing away unbound phage, and eluting specifically bound phage by disrupting the binding interactions between the phage and the target. A portion of the eluted phage is set aside for DNA sequencing and peptide identification, and the remainder is amplified in vivo to prepare a sub-library for the next round. Then, this procedure is repeated.

Therefore, the present invention provides a method of selecting peptides binding to the volatile organic compound, including: providing a peptide-displaying phage library; reacting the phage library with the volatile organic compound; removing phages that are unbound in the reaction; and selecting phages that bind to the volatile organic compound from the phage library; and further including: amplifying the selected phages in a host cell to repeat the above procedure, and isolating amplified or replicated phages, or expressed peptides.

In the method of selecting the peptide binding to the graphitic material, the phage may be M13 phage, F1 phage, Fd phage, If1 phage, Ike phage, Zj/Z phage, Ff phage, Xf phage, Pf1 phage or Pf3 phage, and the peptide library may be, for example, p8 peptide library of M13 phage.

In an exemplary embodiment, since a phage has about 2700 copies of the p8 protein, the p8 peptide library may be efficiently amplified, and no additional protein purification process is needed.

Another aspect of embodiments provide a device for detecting or eliminating a volatile organic compound, wherein the device includes the peptide or peptide set.

The detecting or eliminating device may further include a substrate. The peptide or peptide set according to an exemplary embodiment may be immobilized onto the substrate. Further, the detecting or eliminating device may include a substrate onto which the phage displaying the peptide or peptide set according to an exemplary embodiment on the coat protein of the phage or the fragment thereof, or the graphitic material bound with the peptide or peptide set or the phage is immobilized or coated.

The substrate may be a conductive substrate or an insulating substrate. In some embodiments, the substrate may be an insulating substrate with at least one electrode thereon. The at least one electrode may include at least one electrode selected from a first electrode, a second electrode, and a third electrode. In some embodiments, the at least one electrode may include at least one electrode selected from a working electrode, an opposite electrode, and a reference electrode. The at least one electrode may further include, in addition to the working electrode, the opposite electrode, and the reference electrode, at least one electrode selected from an auxiliary electrode and a recognition electrode.

Examples of the substrate may include a silver substrate, a silver epoxy substrate, a palladium substrate, a copper substrate, a gold substrate, a platinum substrate, a silver/silver chloride substrate, a silver/silver ion substrate, a mercury/mercury oxide substrate, a conductive carbon substrate, a semiconductor substrate, an oxide substrate, and a polymer substrate.

The substrate may be also a transparent flexible substrate. Examples of the transparent flexible substrate may include substrates that are manufactured from polydimethylsiloxane (PDMS), polyethersulfone (PES), poly(3,4-ethylenedioxythiophene), poly(styrenesulfonate), polyimide, polyurethane, polyester, perfluoropolyether (PFPE), polycarbonate, or combinations thereof.

Figure 7:
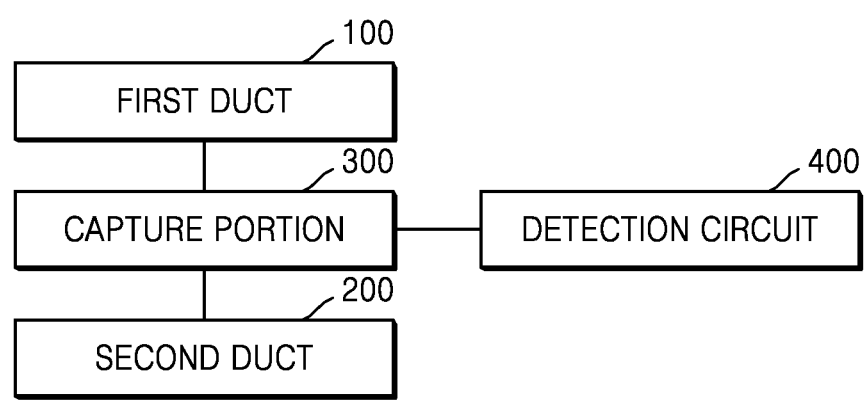
FIG. 7 is a schematic illustration showing a structure of a device for detecting or eliminating volatile organic compounds according to an exemplary embodiment.

Referring to FIG. 7, the device for detecting or eliminating a volatile organic compound may include a first duct 100, a second duct 200, and an capture portion 300.

The first duct 100 has a flow channel therein through which a sample enters. The first duct 100 may be a micro channel or a micro flow channel. The first duct 100 may include a first tube, a second tube, or a third tube, and the first tube may be connected to, for example, a facility or the mouth of an animal, through which the sample enters. The sample may be air or a liquid. The second tube may be connected to a rear end of the first tube, and the third tube may be connected to a rear end of the second tube. The third tube may include a first portion having a diameter equal to that of the second tube, and a second portion that is conical such that the diameter thereof gradually increases toward a read end thereof.

The device may include a pre-treatment portion that may be either located inside or connected to the first duct 100. The capture portion 300 may be disposed on the rear side of the first duct 100. The pre-treatment portion may be used to regulate the moisture of a sample entering the first duct 100 or remove dust. An example of the pre-treatment portion may include a moisture supply portion configured to supply moisture into the first duct 100, a moisture sensor configured to measure the moisture of a sample passing through the first duct 100, or a filter configured to remove dust included in contaminated air. The filter may be used to remove a solid component or a foreign material included in the sample, and may be a fibrous filter.

The capture portion 300 may detect or remove a volatile organic compound, and may include a sensor including a substrate on which the peptide or peptide set, or the phage is immobilized.

Figure 8:
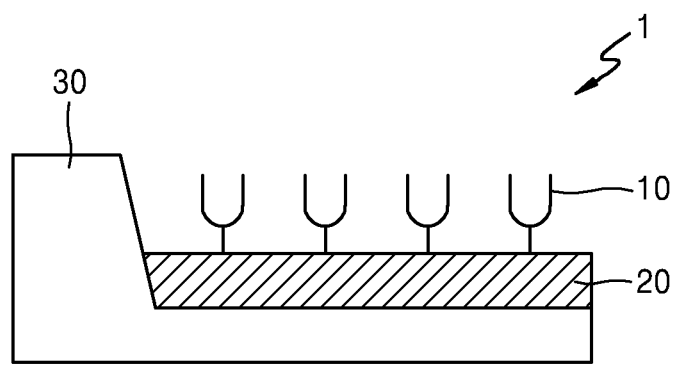
FIG. 8 is a schematic illustration showing a sensor of the device for detecting or eliminating volatile organic compounds according to an exemplary embodiment.

Referring to FIG. 8, an example of an capture portion may be a cantilever sensor 30. In this regard, a volatile organic compound binding layer 10, for example, a peptide or phage according to an embodiment may be immobilized on the cantilever sensor 30 through a substrate 20. The substrate 20 is already described above. The cantilever sensor 30 may be in a dynamic mode in which change in a resonance frequency number expressed by the change in mass and spring constant is measured, or a static mode in which a displacement that occurs due to the change in surface stress caused by a specific reaction on a cantilever sensor is measured. The cantilever sensor 30 may further include a circuit that measures a warp phenomenon or the change in resonance frequency number of the sensor, a piezoelectric sensor that converts a state of the cantilever sensor 30 that has been changed due to vibrations into an electric sensing signal, or a circuit that measures the change in a unique vibration number of the cantilever sensor 30 through the electric sensing signal.

During a sample passes through the capture portion 300, a volatile organic compound included in the sample may be detected by the detection circuit 400. The term "detection of a volatile organic compound" used herein may include qualitative, semi-quantitative, and quantitative detections of a volatile organic compound included in a sample. Qualitative evaluation results show whether a volatile organic compound is detected in a sample. Semi-quantitative evaluation results show whether an amount of a volatile organic compound included in a sample is equal to or greater than a certain boundary level. Quantitative evaluation results show a positive numeral indication of a volatile organic compound included in a sample.

The second duct 200 is connected to the rear side of the capture portion 300. The second duct 200 may be a micro channel or a micro flow channel. The second duct 200 may include a fourth tube and a fifth tube. The fourth tube may have a structure that is symmetric to that of the third tube. That is, the fourth tube may include a third portion having a diameter equal to that of the second portion; a fourth portion that is formed at a rear end of the third portion and conical such that the diameter thereof gradually decreases toward the read end thereof; and a fifth portion that is formed on a read end of the fourth portion.

The fifth tube is connected to the fifth portion of the fourth tube, extending in a certain length. A ventilation fan may be installed at the fifth portion. The ventilation fan may be connected to a motor installed outside the second duct 200. Due to the ventilation fan, the sample enters the first duct 100 and is discharged to the outside through the second duct 200. In this regard, the volatile organic compound in the sample may be detected or eliminated while passing through the capture portion 300.

Still another aspect provides a method of detecting or eliminating a volatile organic compound present in a sample, including contacting the sample with the peptide or peptide set or the phage.

The detecting method may include providing the sample to be analyzed; contacting the sample with the peptide or peptide set, the phage, or the graphitic material; or detecting a volatile organic compound-peptide complex present in the sample from the contacted sample.

Further, the eliminating method may include providing the sample to be analyzed; contacting the sample with the peptide or peptide set, the phage, or the graphitic material; or eliminating the volatile organic compound-peptide complex present in the sample from the contacted sample, after formation of the complex.

The sample to be analyzed may be a sample suspected of containing the volatile organic compound, and may include a liquid, air, or human exhaled breath.

The contacting is to bind the volatile organic compound present in the sample with the peptide or the peptide set, and to mix the peptide or peptide set with the sample. The mixing may be performed by applying the sample to the substrate, onto which the peptide or peptide set is immobilized. Further, the mixing may be performed in a liquid medium or the air. The liquid medium may include a buffer, a solvent or distilled water.

The detecting is to detect the presence or absence of the volatile organic compound in the sample, and it may be performed to detect the volatile organic compound in the sample, qualitatively, semi-quantitatively, and quantitatively. The detecting may be performed by an electrochemical, optical, or mass spectrometric method. The detecting by the electrochemical method may include sensing and measuring the electron transfer which occurs before and after contacting of the sample with the peptide, that is, before and after binding of the volatile organic compound with the peptide. The detecting by the optical method may include labeling the peptide with a fluorescent material to measure fluorescence of the volatile organic compound-peptide complex. The detecting by the mass spectrometric method may include analyzing a difference in the mass spectra acquired before and after contacting of the sample with the peptide, that is, before and after binding of the volatile organic compound with the peptide.

The composition, device or method of detecting the volatile organic compound according to an exemplary embodiment may be used to detect the presence or absence of the volatile organic compounds present in human exhaled breath, thereby being utilized as a sensor for diagnosing diseases. For example, volatile organic compounds (e.g., benzene or toluene, etc.) are detected in exhaled breath of patients with lung cancer. Therefore, the composition, device or method of detecting the volatile organic compound according to an exemplary embodiment may be applied to a diagnostic sensor for diseases, for example, a diagnostic kit for lung cancer, a diagnostic sensor for lung cancer, or a diagnostic method for lung cancer.

Hereinafter, the present invention will be described in more detail with reference to Examples. However, these Examples are for illustrative purposes only, and the invention is not intended to be limited by these Examples.

Example 1

Screening of Peptides Selectively Binding to Volatile Organic Compounds

1. Preparation of M13 Phage Display p8 Peptide Library

To screen peptides which selectively bind to volatile organic compounds, an M13 phage display p8 peptide library is prepared.

First, an M13HK vector is prepared using oligonucleotides of SEQ ID NOS. 34 and 35 for site-directed mutation of the 1381st base pair C of an M13KE vector (NEB, product#N0316S) (SEQ ID NO: 33) to G. The prepared M13HK vector is double-digested using restriction enzymes, BspHI (NEB, product# R0517S) and BamHI (NEB, product#R3136T), and dephosphorylated using antarctic phosphatase. The dephosphorylated vector is ligated to a double-digested DNA duplex by incubation at 16° C. overnight. A product is then purified and concentrated. Electrocompetent cells (XL-1 Blue, Stratagene) are transformed with 2 µl of a concentrated ligated vector solution by electroporation at 18 kV/cml. A total of five transformations are performed for the library construction. Then, the transformed cells are incubated for 60 minutes, and fractions of several transformants are plated onto agar plates containing x-gal/isopropyl-β-D-1-thiogalactopyranoside (IPTG)/tetracycline (Tet) to determine the diversity of the library. The remaining cells are amplified in a shaking incubator for 8 hours. In the preparation of the phage display p8 peptide library, oligonucleotides of SEQ ID NOS. 36 and 37 are used.

The nucleotide sequences of the phage display p8 peptide library constructed according to a specific embodiment have diversity of $4.8 \times 10^7$ pfu (plaque forming unit), and include approximately $1.3 \times 10^5$ copies of each sequence.

FIG. 1 is a schematic illustration showing a structure of M13 phage according to a specific embodiment.

As shown in FIG. 1, M13 phage has a length of about 880 nm and a diameter of about 6.5 nm, and consists of single stranded DNA of 6407 nucleotides, which is wrapped by the major coat protein of p8 protein (50 amino acid residues) with 2700 copies, and the minor coat proteins of p3 (427 amino acid residues), p6 (112 amino acid residues), p7 (33 amino acid residues), and p9 (32 amino acid residues) with 5 copies or smaller. The peptide library according to a specific embodiment displays by replacement of the amino acid sequence at positions of 2 to 4 (i.e., EGD) of p8.

2. Screening of Peptide 2.1. Screening of Peptide 1

The phage-display p8 peptide library prepared in 1 of Example 1 is used to screen peptides selectively binding to benzene by a bio-panning method.

First, a molecule having a thiol group at one end and a phenyl group (benzene) at the other end is prepared. The prepared molecule is immobilized onto a gold surface by a gold thiol bond so as to prepare a benzene-immobilized SAM (Self-Assembled Monolayer) chip (diameter of 1 cm). Subsequently, the phage display p8 peptide library of $1 \times 10^{10}$ pfu ($1 \times 10^7$ pfu diversities,) prepared in 1 of Example 1 is added to 100 µL of Tris-buffered saline (TBS). To remove background phages, the phage solution is reacted with tri(ethylene glycol)-terminated alkanthiols (TEG) chip and a supernatant is conjugated with the prepared benzene-immobilized surface for 1 hour in a shaking incubator at 50 rpm at room temperature (positive selection). 1 hour later, the solution on the surface is partially removed and washed with 1 mL of TBS 10 times (100 rpm) to remove phages that displays non-selectively reacting peptides. Then, the substrate is reacted with 80 µl of 0.2 M glycine-HCl at pH 2.2 for 8 minutes to elute phages that display peptides selectively reacting with benzene, and carefully transferred to a 1.5 mL-microcentrifuge tube, and immediately neutralized with 20 µl of 1 M Tris-HCl at pH 9.3. To obtain phages displaying selective peptides, which could not be obtained by the buffer at pH 2.2, the buffer-removed chip is incubated in *E. coli* solution (OD 600:0.4) for 30 minutes to elute phages. The eluted phages are amplified and then the above procedure is repeated twice. To determine the number of phages to be supplied at each round of panning, the number of phages eluted and amplified is measured in plaque-forming units (PFU) using agar plates containing x-gal/isopropyl-β-D-1-thiogalactopyranoside (IPTG)/tetracycline. Further, the plaques of each round are amplified to analyze DNA sequences so as to obtain a peptide sequence reacting with benzene, BP1 (SEQ ID NO: 17), BP2 (SEQ ID NO: 18), BP3 (SEQ ID NO: 19), BP4 (SEQ ID NO: 20), BP5 (SEQ ID NO: 21), BP6 (SEQ ID NO: 22), BP7 (SEQ ID NO: 23), BP8 (SEQ ID NO: 24), BP9 (SEQ ID NO: 25), BP10 (SEQ ID NO: 26), BP11 (SEQ ID NO: 27), or BP12 (SEQ ID NO: 28).

The amino acid sequences of the peptides screened by the biopanning method exhibit hydrophobic property at the C-terminus, suggesting that the peptides bind with hydrophobic benzene by hydrophobic interaction.

2.2. Screening of Peptide 2

Peptides selectively binding to toluene are screened in the same manner as in 2.1 of Example 1, except that a molecule having a tolyl group is prepared and used to prepare a toluene-immobilized SAM chip. As a result, peptide sequences reacting with toluene, TP1 (SEQ ID NO: 29), TP2 (SEQ ID NO: 30), TP3 (SEQ ID NO: 31), and TP4 (SEQ ID NO: 32) are obtained.

The amino acid sequences of the peptides screened by the biopanning method exhibit hydrophobic property at the C-terminus, suggesting that the peptides bind with hydrophobic toluene by hydrophobic interaction.

3. Test of Reactivity of Volatile Organic Compound in Liquid Phase and Gas Phase 3.1. Test of Reactivity in Liquid Phase To examine whether the peptide screened in 2.1 of Example 1, BP1 selectively reacts with a volatile organic compound benzene, its binding affinity in liquid phase is analyzed.

First, a phage displaying the BP1 (SEQ ID NO: 17) peptide is prepared at a concentration of $10^9$/100 µl. 100 µl of the phage solution is conjugated with the benzene chip for 1 hour in a shaking incubator at 50 rpm at room temperature (positive selection). 1 hour later, the solution on the surface is partially removed and washed with 1 mL of TBS 5 times (100 rpm). Then, the washed substrate is reacted with 80 µl of 0.2 M glycine-HCl at pH 2.2 for 8 minutes, and carefully transferred to a 1.5 mL-microcentrifuge tube, and immediately neutralized with 20 µl of 1 M Tris-HCl at pH 9.3. The number of phages in the neutralized solution is measured in plaque-forming units (PFU) using agar plates containing x-gal/isopropyl-β-D-1-thiogalactopyranoside (IPTG)/tetracycline, and the result is shown in FIG. 2.

Further, to examine whether the peptide sequences screened in 2.1 of Example 1 (SEQ ID NO: 17), BP2 (SEQ ID NO: 18), BP3 (SEQ ID NO: 19), BP4 (SEQ ID NO: 20), BP5 (SEQ ID NO: 21), BP6 (SEQ ID NO: 22), BP7 (SEQ ID NO: 23), BP8 (SEQ ID NO: 24), BP9 (SEQ ID NO: 25), BP10 (SEQ ID NO: 26), BP11 (SEQ ID NO: 27), and BP12 (SEQ ID NO: 28) react with a volatile organic compound benzene, their binding affinity in liquid phase is analyzed in the same manner as above. The result is shown in FIG. 3.

Further, to examine whether the peptide sequences screened in 2.2 of Example 1, TP1 (SEQ ID NO: 29), TP2 (SEQ ID NO: 30), TP3 (SEQ ID NO: 31), and TP4 (SEQ ID NO: 32) react with a volatile organic compound, benzene or toluene, their binding affinity in liquid phase is analyzed. The analysis is performed in the same manner as above, except that their binding affinity is analyzed in the toluene chip as well as in the benzene chip. The result is shown in FIG. 4.

Figure 2:
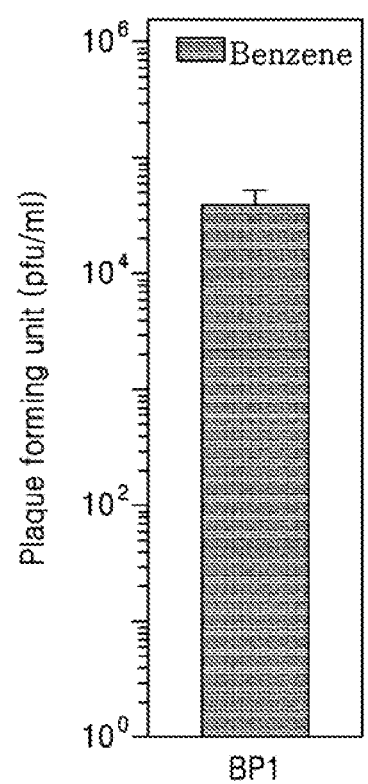
FIG. 2 is a result of analyzing binding affinity of a peptide according to a specific embodiment, BP1 (SEQ ID NO: 17) for a volatile organic compound in liquid phase.
Figure 3:
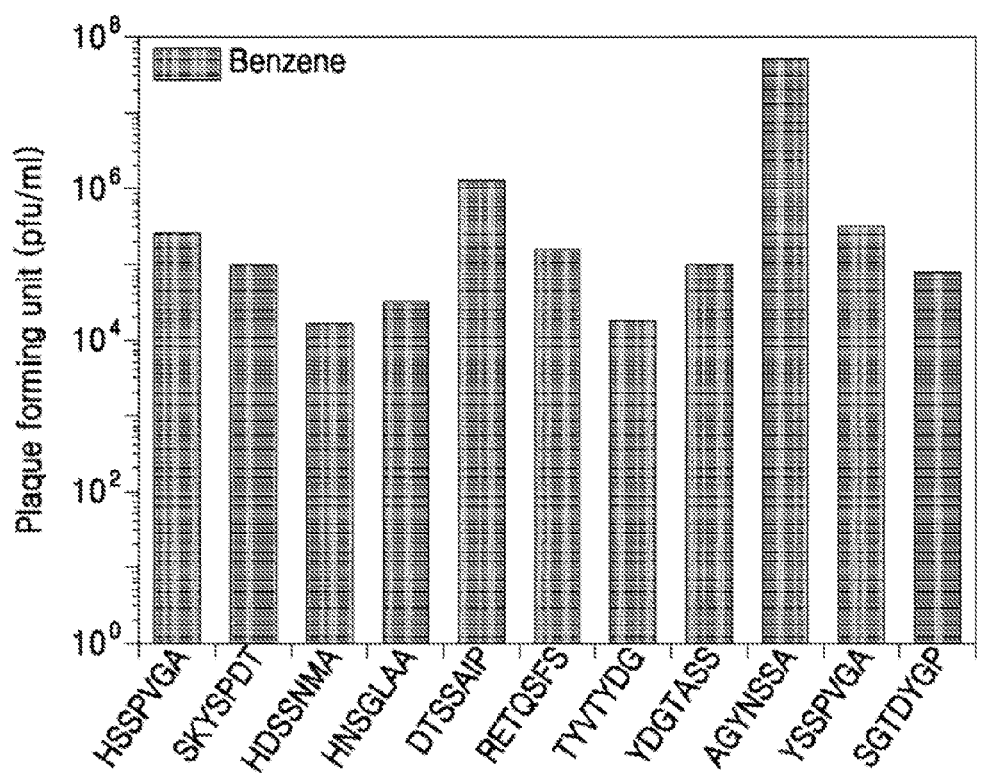
FIG. 3 is a result of analyzing binding affinity of the peptide according to a specific embodiment for volatile organic compounds in liquid phase.
Figure 4:
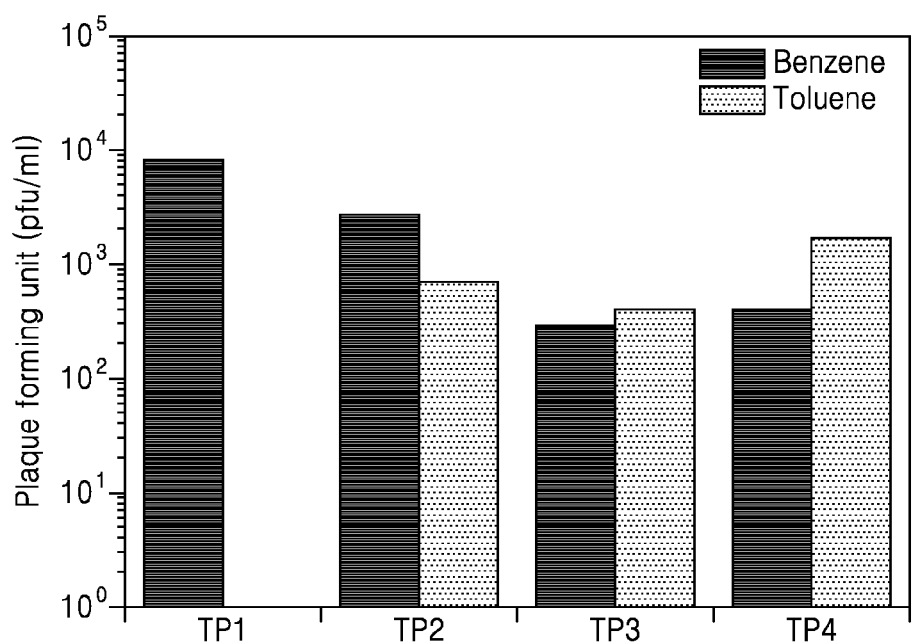
FIG. 4 is a result of analyzing binding affinity of the peptide according to a specific embodiment for volatile organic compounds in liquid phase.

FIGS. 2 through 4 are results of analyzing binding affinity of the peptides according to a specific embodiment for volatile organic compounds in liquid phase.

As shown in FIG. 2, the peptide according to a specific embodiment, BP1 (SEQ ID NO: 17) exhibits binding affinity for benzene in liquid phase.

As shown in FIG. 3, the peptides according to a specific embodiment, BP2 (SEQ ID NO: 18), BP3 (SEQ ID NO: 19), BP4 (SEQ ID NO: 20), BP5 (SEQ ID NO: 21), BP6 (SEQ ID NO: 22), BP7 (SEQ ID NO: 23), BP8 (SEQ ID NO: 24), BP9 (SEQ ID NO: 25), BP10 (SEQ ID NO: 26), BP11 (SEQ ID NO: 27), and BP12 (SEQ ID NO: 28) exhibit binding affinity for benzene.

As shown in FIG. 4, the peptides according to a specific embodiment, TP1 (SEQ ID NO: 29), TP2 (SEQ ID NO: 30), TP3 (SEQ ID NO: 31), and TP4 (SEQ ID NO: 32) exhibit binding affinity for benzene or toluene.

3.2. Test of Reactivity in Gas Phase

To examine whether the peptide screened in 2.1 of Example 1, BP1 (SEQ ID NO: 17) selectively reacts with 6 kinds of volatile organic compounds, its binding affinity in gas phase is analyzed using a microcantilever system.

Cantilevers in the fourth compartment are used as references. For peptide immobilization, Cr (10 nm)/Au (50 nm) layers are deposited onto the microcantilevers. The surface is cleaned in piranha solution (4:1 ratio of $H_2SO_4$ (98.08%) and $H_2O_2$ (34.01%)) to remove any contaminants present on the surface, and then rinsed with deionized water. Thiolated peptides (50 µL of 10 µM solution) are immobilized on the gold surface of cantilevers at room temperature for 5 hours. The peptide-conjugated microcantilevers are rinsed with DI/ethanol and dried under nitrogen. For measurements, the peptide-conjugated microcantilevers are enclosed within a chamber containing an inlet and an outlet for the gas flow. Moisture during measurements is monitored with an integrated sensor in the chamber. The flow rate of all gases is controlled at 100 standard cubic centimeter per minute (sccm) using a mass flow controller (MFC). Before the measurement, the microcantilevers are stabilized by nitrogen at 100 sccm overnight. Then, 6 kinds of gases including benzene, toluene, xylene, hexane, acetone, and ethanol are injected to test reactivity, respectively. In this regard, a reaction time is 10 minutes, and a $N_2$ purging time is 25 minutes. Gas injection is conducted in this order of benzene (4032 ppm), toluene (5026 ppm), xylene (6039 ppm), hexane (5299 ppm), acetone (8798 ppm), and ethanol (1473 ppm), and the results are shown in FIGS. 5 and 6.

Figure 5:
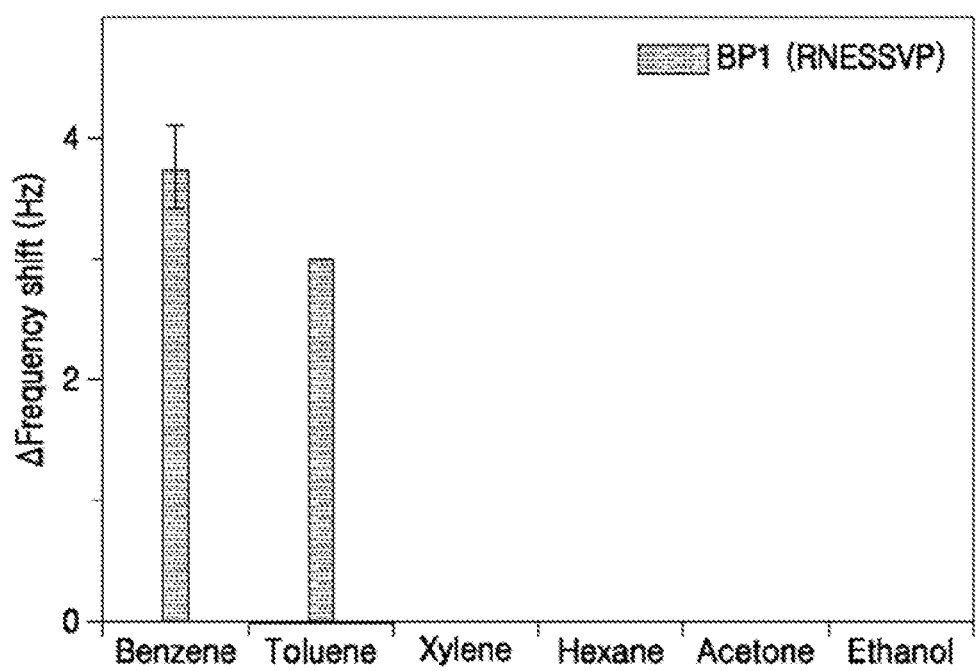
FIG. 5 is a result of analyzing binding affinity of the peptide according to a specific embodiment for volatile organic compounds in gas phase.

FIG. 5 is a result of analyzing binding affinity of the peptide according to a specific embodiment for volatile organic compounds in gas phase.

Figure 6:
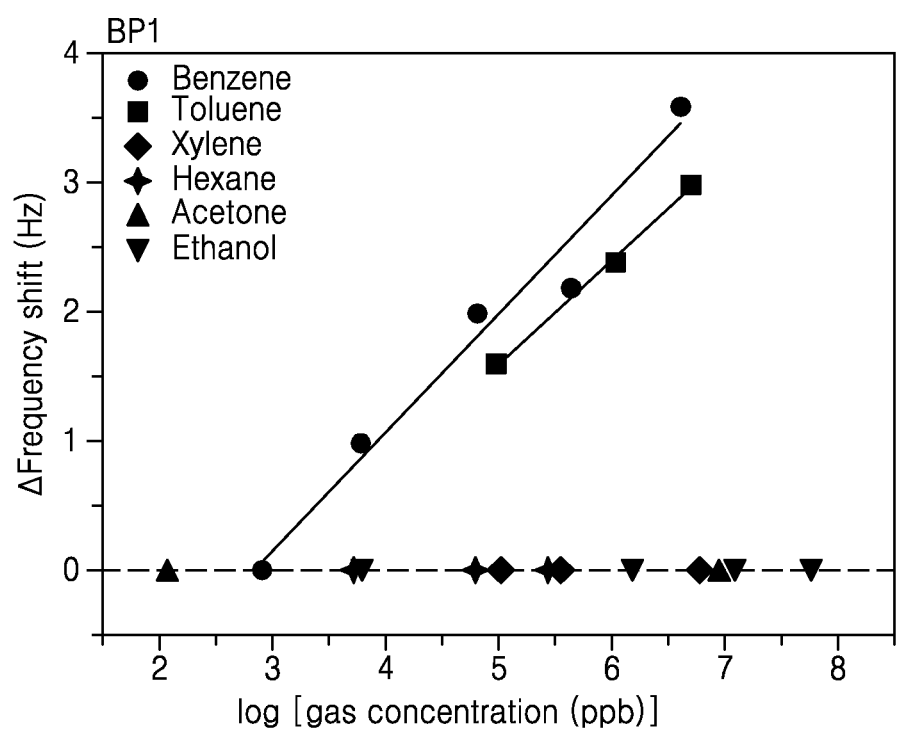
FIG. 6 is a result of quantitatively analyzing volatile organic compounds according to concentrations, in which the volatile organic compounds are collected by the peptide according to a specific embodiment (B: benzene, T: toluene, X: xylene, H: hexane, A: acetone, E: ethanol)

FIG. 6 is a result of quantitatively analyzing volatile organic compounds according to concentrations, in which the volatile organic compounds are collected by the peptide according to a specific embodiment (B: benzene, T: toluene, X: xylene, H: hexane, A: acetone, E: ethanol).

As shown in FIG. 5, the peptide according to a specific embodiment, BP1 (SEQ ID NO: 17) is able to selectively bind to benzene and toluene in gas phase.

As shown in FIG. 6, the peptide according to a specific embodiment, BP1 (SEQ ID NO: 17) is able to effectively collect benzene and toluene in gas phase, which is consistent with the result of FIG. 5.

A peptide according to an aspect has excellent selectivity for volatile organic compounds and has stability at room temperature so as to effectively collect and detect or eliminate volatile organic compounds.

What is claimed is:

1. A peptide or peptide set consisting of one or more amino acid sequences selected from the group consisting of SEQ ID NOs: 17-32, wherein the peptide consisting of the amino acid sequence of any one of SEQ ID NOs: 17-32 binds to benzene, and the peptide consisting of the amino acid sequence of any one of SEQ ID NOs: 17 and 30-32 binds to toluene.

2. The peptide or peptide set of claim 1, wherein the peptide or peptide set is displayed on a coat protein of a phage or a fragment thereof.

3. The peptide or peptide set of claim 2, wherein the phage is M13 phage, F1 phage, Fd phage, If1 phage, Ike phage, Zj/Z phage, Ff phage, Xf phage, Pf1 phage, or Pf3 phage.

4. The peptide or peptide set of claim 2, wherein the C-terminus of the peptide or peptide set is linked to the N-terminus of the coat protein of the phage, or the peptide or peptide set is inserted between consecutive amino acid sequences of the coat protein of the phage or replaces the consecutive amino acid sequences of the coat protein.

5. The peptide or peptide set of claim 2, wherein the coat protein is selected from the group consisting of p3, p6, p8 and p9 of M13 phage.

6. A method of detecting benzene in a sample, the method comprising contacting the sample with a peptide or peptide set consisting of one or more amino acid sequences selected from the group consisting of SEQ ID NOs: 17-32.

7. A method of detecting toluene in a sample, the method comprising contacting the sample with a peptide or peptide set consisting of one or more amino acid sequences selected from the group consisting of SEQ ID NOs: 17 and 30-32.

* * * * *